(12) United States Patent
Davis, III et al.

(10) Patent No.: US 7,708,755 B2
(45) Date of Patent: *May 4, 2010

(54) STRETCH RESISTANT EMBOLIC COIL DELIVERY SYSTEM WITH COMBINED MECHANICAL AND PRESSURE RELEASE MECHANISM

(75) Inventors: Richard Champion Davis, III, Plantation, FL (US); John H. Thinnes, Jr., Miami Beach, FL (US)

(73) Assignee: Codman & Shurtleff Inc., Raynham, MA (US)

( * ) Notice: Subject to any disclaimer, the term of this patent is extended or adjusted under 35 U.S.C. 154(b) by 158 days.

This patent is subject to a terminal disclaimer.

(21) Appl. No.: 11/765,568

(22) Filed: Jun. 20, 2007

(65) Prior Publication Data

US 2007/0270903 A1  Nov. 22, 2007

Related U.S. Application Data

(63) Continuation-in-part of application No. 11/301,865, filed on Dec. 12, 2005, now Pat. No. 7,367,987, which is a continuation-in-part of application No. 11/143,052, filed on Jun. 2, 2005, now Pat. No. 7,371,251.

(51) Int. Cl.
*A61M 29/00* (2006.01)
*A61F 2/06* (2006.01)
(52) U.S. Cl. .................... 606/200; 606/191; 623/1.11
(58) Field of Classification Search .............. 606/142, 606/151, 191, 200, 213; 623/1.1, 1.11
See application file for complete search history.

(56) References Cited

U.S. PATENT DOCUMENTS 5,108,407 A  4/1992  Geremia et al.

5,122,136 A  6/1992  Gugliemi et al.

(Continued)

FOREIGN PATENT DOCUMENTS

EP  754435 A1  1/1997

(Continued)

OTHER PUBLICATIONS

European Search Report EP 06 25 2708 dated Sep. 11, 2006 with Annex to the European Search Report.

(Continued)

*Primary Examiner*—Julian W Woo
*Assistant Examiner*—Melissa Ryckman
(74) *Attorney, Agent, or Firm*—Cook Alex Ltd.

(57) ABSTRACT

A medical device for placing an embolic device at a predetermined site within a vessel of the body including a delivery catheter and a flexible pusher member slidably disposed within the lumen of the catheter. A fluid pressure source is coupled to the proximal end of the pusher member. An embolic device is retained at the distal end of the pusher member by a mechanical interlocking mechanism. The distal end of the pusher member includes a spiral ribbon section encircled by a tubular member. The tubular member or the distal end of the pusher member directs fluid from the fluid pressure source against the embolic device. The mechanical interlocking mechanism is disengaged from the embolic device and a fluid pressure is applied against the embolic device to ensure the release of the embolic device.

14 Claims, 6 Drawing Sheets

U.S. PATENT DOCUMENTS

| | | |
|---|---|---|
| 5,250,071 A | 10/1993 | Palermo |
| 5,263,964 A | 11/1993 | Purdy |
| 5,334,210 A | 8/1994 | Gianturco |
| 5,350,397 A | 9/1994 | Palermo et al. |
| 5,382,259 A | 1/1995 | Phelps et al. |
| 5,540,680 A | 7/1996 | Gugliemi et al. |
| 5,582,619 A | 12/1996 | Ken |
| 5,601,600 A | 2/1997 | Ton et al. |
| 5,800,455 A | 9/1998 | Palermo et al. |
| 5,853,418 A | 12/1998 | Ken et al. |
| 5,895,391 A | 4/1999 | Famholz |
| 5,895,411 A | 4/1999 | Irie |
| 5,925,059 A * | 7/1999 | Palermo et al. ............ 606/191 |
| 6,113,622 A * | 9/2000 | Hieshima ................... 606/200 |
| 6,193,728 B1 | 2/2001 | Ken et al. |
| 6,203,547 B1 | 3/2001 | Nguyen et al. |
| 6,238,415 B1 | 5/2001 | Sepetka et al. |
| 6,361,547 B1 | 3/2002 | Hieshima |
| 6,500,149 B2 | 12/2002 | Gandhi et al. |
| 6,537,314 B2 | 3/2003 | Langberg et al. |
| 6,544,225 B1 | 4/2003 | Lulo et al. |
| 6,554,849 B1 | 4/2003 | Jones et al. |
| 6,607,538 B1 | 8/2003 | Ferrera et al. |
| 6,660,020 B2 | 12/2003 | Wallace et al. |
| 6,689,141 B2 | 2/2004 | Ferrera et al. |
| 6,793,673 B2 | 9/2004 | Kowalsky et al. |
| 6,811,561 B2 | 11/2004 | Diaz et al. |
| 6,835,185 B2 | 12/2004 | Ramzipoor |
| 6,849,303 B2 | 2/2005 | Dave |
| 6,902,572 B2 | 6/2005 | Beulke |
| 6,958,068 B2 | 10/2005 | Hieshima |
| 6,966,914 B2 | 11/2005 | Abe |
| 6,994,711 B2 | 2/2006 | Hieshima et al. |
| 7,367,987 B2 * | 5/2008 | Balgobin et al. ............ 606/200 |
| 7,371,251 B2 * | 5/2008 | Mitelberg et al. ........... 606/200 |
| 7,371,252 B2 * | 5/2008 | Balgobin et al. ............ 606/200 |
| 7,377,932 B2 * | 5/2008 | Mitelberg et al. ........... 606/200 |
| 2001/0002438 A1 | 5/2001 | Sepetka et al. |
| 2002/0111647 A1 | 8/2002 | Khairkhahan et al. |
| 2002/0165569 A1 | 11/2002 | Ramzipoor et al. |
| 2004/0034363 A1 | 2/2004 | Wilson et al. |
| 2004/0044361 A1 | 3/2004 | Frazier et al. |
| 2004/0111095 A1 | 6/2004 | Gordon et al. |
| 2005/0043755 A1 | 2/2005 | Wilson et al. |
| 2005/0113864 A1 | 5/2005 | Gandhi et al. |
| 2006/0276823 A1 | 12/2006 | Mitelberg et al. |
| 2006/0276824 A1 * | 12/2006 | Mitelberg et al. ........... 606/200 |
| 2006/0276825 A1 * | 12/2006 | Mitelberg et al. ........... 606/200 |
| 2006/0276826 A1 * | 12/2006 | Mitelberg et al. ........... 606/200 |
| 2006/0276827 A1 * | 12/2006 | Mitelberg et al. ........... 606/200 |
| 2006/0276828 A1 * | 12/2006 | Balgobin et al. ............ 606/200 |
| 2006/0276829 A1 | 12/2006 | Balgobin et al. |
| 2006/0276830 A1 * | 12/2006 | Balgobin et al. ............ 606/200 |
| 2006/0276832 A1 * | 12/2006 | Balgobin et al. ............ 606/200 |
| 2006/0276833 A1 | 12/2006 | Balgobin et al. |
| 2006/0276834 A1 * | 12/2006 | Balgobin et al. ............ 606/200 |
| 2007/0010849 A1 | 1/2007 | Balgobin et al. |
| 2007/0010850 A1 | 1/2007 | Balgobin et al. |
| 2007/0118172 A1 | 5/2007 | Balgobin |

FOREIGN PATENT DOCUMENTS

| | | |
|---|---|---|
| EP | 832607 A1 | 4/1998 |
| EP | 832607 B1 | 8/2000 |
| EP | 754435 B1 | 12/2003 |
| WO | WO 96/38092 | 12/1996 |
| WO | WO 2004/008974 | 1/2004 |

OTHER PUBLICATIONS

European Search Report EP 06 25 6285 dated Feb. 26, 2007 with Annex to European Search Report.

* cited by examiner

STRETCH RESISTANT EMBOLIC COIL DELIVERY SYSTEM WITH COMBINED MECHANICAL AND PRESSURE RELEASE MECHANISM

CROSS-REFERENCE TO RELATED APPLICATION(S)

This patent application is a continuation-in-part of U.S. patent application Ser. No. 11/301,865, filed on Dec. 12, 2005, entitled, "Stretch Resistant Embolic Coil Delivery System With Mechanical Release Mechanism," which is a continuation-in-part of U.S. patent application Ser. No. 11/143,052, filed on Jun. 2, 2005, entitled, "Stretch Resistant Embolic Coil Delivery System With Mechanical Release Mechanism."

BACKGROUND OF THE INVENTION

1. Field of the Invention

The present invention relates to a medical device for placing a stretch resistant embolic device at a predetermined site within a vessel of the human body, and more particularly, relates to a catheter-based deployment system for delivering an embolic device. This device is particularly suited to transport an embolic device, such as a stretch resistant embolic coil, through the tortuous vasculature of the human brain to a selected site within the vessel or within an aneurysm.

2. Description of the Prior Art

For many years, flexible catheters have been used to place various devices within the vessels of the human body. Such devices include dilation balloons, radiopaque fluids, liquid medications, and various types of occlusion devices such as balloons and embolic coils. Examples of such catheter-based devices are disclosed in U.S. Pat. No. 5,108,407, entitled, "Method and Apparatus for Placement of an Embolic Coil" and U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents and the other patents and patent applications referenced herein are hereby incorporated herein by reference. These patents disclose catheter-based devices for delivering embolic coils to preselected positions within vessels of the human body in order to treat aneurysms, or alternatively, to occlude blood vessels at a particular location.

Coils which are placed in vessels may take the form of helically wound coils, or alternatively, may take the form of randomly wound coils, coils wound within coils or other such coil configurations. Examples of various coil configurations are disclosed in U.S. Pat. No. 5,334,210, entitled, "Vascular Occlusion Assembly" and U.S. Pat. No. 5,382,259 entitled, "Vasoocclusion Coil with Attached Tubular Woven or Braided Fibrous Covering." Embolic coils are generally formed of a radiopaque metallic material, such as platinum, gold, tungsten, or alloys of these metals. Often, several coils are placed at a given location to occlude the flow of blood through the vessel, or aneurysm, by promoting thrombus formation at the particular site.

In the past, embolic coils have been placed within the distal end of a catheter. When the distal end of the catheter is properly positioned, the coil may then be pushed out of the end of the catheter with a pusher member to release the coil at the desired location. This procedure for placement of an embolic coil is conducted under fluoroscopic visualization such that the movement of the coil through the vasculature of the body may be monitored and the coil placed at the desired location.

Another procedure involves the use of glue or solder for attaching the coil to a guidewire, which in turn, is placed within a flexible catheter for positioning the coil within the vessel at a preselected position. Once the coil is in the desired position, the coil is held in position by the catheter and the guidewire is pulled proximally to thereby cause the coil to become detached from the guidewire and released from the catheter. Such a coil positioning system is disclosed in U.S. Pat. No. 5,263,964 entitled, "Coaxial Traction Detachment Apparatus and Method."

Still another coil positioning procedure is that of having a catheter with a socket at the distal end of the catheter for retaining a ball which is, in turn, bonded to the proximal end of the coil. The ball, which is generally larger in diameter than the outside diameter of the coil, is placed in the socket within the lumen at the distal end of the catheter and the catheter is then moved into a vessel in order to place the coil at a desired position. Once the position is reached, a pusher wire with a piston at the end thereof is pushed distally from the proximal end of the catheter to push the ball out of the socket in order to release the coil at the desired position. Such a system is disclosed in U.S. Pat. No. 5,350,397, entitled, "Axially Detachable Embolic Coil Assembly."

Another procedure for placing an embolic coil within a vessel is that of using a heat releasable adhesive bond for retaining the coil at the distal end of the catheter. One such system uses laser energy transmitted through a fiber optic cable to apply heat to the adhesive bond in order to release the coil from the end of the catheter. Such a procedure is disclosed in U.S. Pat. No. 5,108,407, entitled "Method and Apparatus for Placement of an Embolic Coil."

Yet another coil deployment system incorporates a catheter having a lumen throughout the length of the catheter and a distal tip for retaining the coil for positioning the coil at a preselected site. The distal tip of the catheter is formed of a material which exhibits the characteristic that when the lumen of the catheter is pressurized the distal tip expands radially to release the coil at the preselected site. Such a deployment system is disclosed in U.S. Pat. No. 6,113,622, entitled, "Embolic Coil Hydraulic Deployment System."

Still another coil deployment system incorporates an interlocking mechanism on the coil. The interlocking end on the embolic coil couples with a similar interlocking mechanism on a pusher assembly. A control wire which extends through the locking mechanism secures the coil to the pusher assembly. The pusher assembly and embolic coil are initially disposed within the lumen of a catheter. When the embolic coil is pushed out of the end of the catheter for placement, the control wire is retracted and the coil disengages from the pusher assembly. Such a deployment system is disclosed in U.S. Pat. No. 5,925,059, entitled, "Detachable Embolic Coil Assembly."

Yet another coil deployment system incorporates an embolic device detachably mounted on the distal portion of a pusher member and held in place with a connector thread or fiber. The fiber passes through a cutter member that may be activated to cut the connector fiber. Once the connector fiber is cut, the embolic device is released. Such a deployment system is disclosed in Published U.S. Patent Application No. 2002/0165569, entitled, "Intravascular Device Deployment Mechanism Incorporating Mechanical Detachment."

Still another coil deployment system incorporates an embolic device with a stretch resistant member therethrough. The distal end of the stretch resistant member attaches to the embolic coil and the proximal end of the stretch resistant member is detachably mounted on the pusher member through various means such as adhesive, or by a connector fiber adhered to or tied to the pusher member, and is detachable by the application of heat. Such a deployment system is disclosed in Published U.S. Patent Application No. 2004/0034363, entitled, "Stretch Resistant Therapeutic Device."

Still another coil deployment system incorporates a pusher wire with a stiff wavy-shaped end segment which is coupled to the embolic coil and is placed in the lumen of the catheter. The coil is advanced through the catheter until it reaches a predetermined site in the vessel at which time the pusher wire is retracted and the embolic coil is released. Such a system is disclosed in U.S. Pat. No. 6,203,547, entitled, "Vaso-occlusion Apparatus Having A Manipulable Mechanical Detachment Joint And A Method For Using The Apparatus."

A still further embolic device deployment system for placement of an embolic device, or coil, includes a delivery catheter and a flexible pusher member. The embolic device is retained by an interlocking mechanism which includes a detachment member which extends through an aperture in an engagement member. The engagement member engages a ring on the embolic device. When the detachment member is withdrawn from the aperture, the embolic device is released. One such deployment system is disclosed in Published U.S. Patent Application No. 2006/0276823, entitled, "Embolic Coil Delivery System With Mechanical Release Mechanism," and assigned to the same assignee as the present application.

Other known methods of deploying an embolic device to a body vessel include those which are pressure-based, rather than being mechanical in nature. For example, in one exemplary system, a flexible catheter has a distal section in which the proximal end of an embolic device is received in a fluid-tight relationship. Upon the application of fluid pressure to the lumen of the catheter (typically by a syringe), the distal section of the catheter will radially expand, thereby releasing the embolic device. Such a system is described in U.S. Pat. No. 6,113,622, entitled, "Embolic Coil Hydraulic Deployment System," and assigned to the same assignee as the present application. Other known pressure-based deployment systems are described in U.S. Pat. Nos. 6,361,547; 6,544,225; 6,607,538; 6,689,141; 6,811,561; 6,958,068; and 6,554,849.

One characteristic of many known pressure-based deployment systems is that they use a flexible catheter to push the embolic device through the vasculature. This stands in contrast to typical embolic device deployment systems wherein an embolic device is pushed through the vasculature by a metallic hypotube guided by a flexible catheter. The use of a hypotube can be desirable due to the superior column strength and pushability of a hypotube, which allows the deployment system to be moved through stenosed regions of a body vessel without buckling or folding back upon itself.

Another characteristic of many known pressure-based deployment systems is that the embolic coil is tightly retained by the catheter or a flexible retention sleeve. The fact that the distal end of the catheter or retention sleeve must radially expand to release the embolic device may limit the outer diameter of the device and/or the diameter to which it can expand, to ensure that the expansion of the catheter or retention sleeve does not harm the surrounding body vessel.

Yet another characteristic of many known pressure-based deployment systems is that they depend on a carefully calibrated fluid seal between the catheter and the embolic device. The catheter must securely hold the embolic device so that it is not prematurely released during delivery, but it must be adapted to release the embolic device at a preselected pressure. Dimensional variations inherent in the manufacturing process create the risk that the fit between the catheter and the embolic device will be too tight or too loose or comprise an incomplete fluid seal. If the catheter holds the embolic device too tightly, it may require more fluid pressure to release the embolic device, which pressure may not be attainable by the syringe or which pressure may endanger the body vessel. If the catheter holds the embolic device too loosely, it may release the embolic device before being delivered to the target site. If an incomplete fluid seal is formed between the catheter or sleeve and the associated embolic device, it may be very difficult or even impossible to develop the necessary pressure to release the embolic device. Even if possible, developing the necessary pressure may take longer than expected, thereby increasing the time required to deploy the embolic device.

With the present approach, it has been determined that characteristics such as these may be less than desirable. The present approach recognizes and addresses shortcomings of these characteristics to provide enhancements not heretofore available.

SUMMARY

In one aspect or embodiment of the present invention, a deployment system is provided for delivering an embolic device to a target location of a body vessel. The system comprises an elongated flexible deployment catheter having a lumen extending therethrough and having proximal and distal ends. An elongated pusher member is slidably disposed within the lumen of the deployment catheter. The pusher member has a distal end, and at least a portion of the distal end comprises a spiral ribbon section. A tubular member engages and substantially encircles an outer surface of the spiral ribbon section. An embolic device is releasably secured to the distal end of the pusher member by a mechanical interlocking mechanism. The tubular member extends distally beyond the distal end of the pusher member to be directly adjacent to or in non-retentive, abutting relationship to a proximal end of the embolic device. A source of fluid pressure is coupled to the proximal end of the pusher member and is in fluid communication with a lumen of the pusher member which, upon actuation, applies fluid pressure to the lumen to thereby move the embolic device away from the pusher member.

According to another aspect or embodiment of the present invention, a deployment system is provided for delivering an embolic device to a target location of a body vessel. The system comprises an elongated flexible deployment catheter having a lumen extending therethrough and having proximal and distal ends. An elongated pusher member is slidably disposed within the lumen of the deployment catheter. The pusher member has a distal end and at least a portion of the distal end comprises a spiral ribbon section. A tubular member engages and substantially encircles an outer surface of the spiral ribbon section. An embolic device is releasably secured to the distal end of the pusher member by a mechanical interlocking mechanism. The distal end of the pusher member extends toward the embolic device to be directly adjacent to or in non-retentive, abutting relationship to a proximal end of the embolic device. A source of fluid pressure is coupled to the proximal end of the pusher member and is in fluid communication with a lumen of the pusher member which, upon actuation, applies fluid pressure to the lumen to thereby move the embolic device away from the pusher member.

According to yet another aspect or embodiment of the present invention, a method is provided for deploying an embolic device to a target location of a body vessel. The method comprises providing a deployment system having an elongated flexible deployment catheter, an elongated pusher member slidably disposed within a lumen of the deployment catheter, a mechanical interlocking mechanism, and an embolic device releasably secured to a distal end of the pusher member by the mechanical interlocking mechanism. The embolic device is positioned generally adjacent to a target location of a body vessel and disengaged from the mechanical interlocking mechanism. Fluid pressure is applied through a lumen of the pusher member against the embolic device, thereby moving the embolic device away from the pusher member.

DESCRIPTION OF THE ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
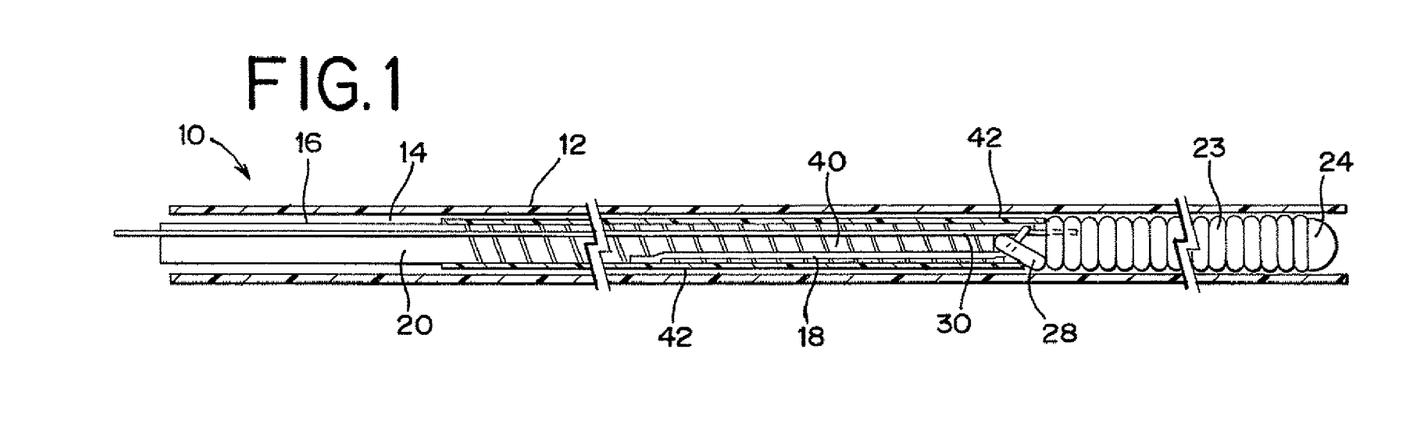
FIG. 1 is a partial cross-sectional view of selected components of an embolic device deployment system according to an aspect of the present invention.
Figure 1A:
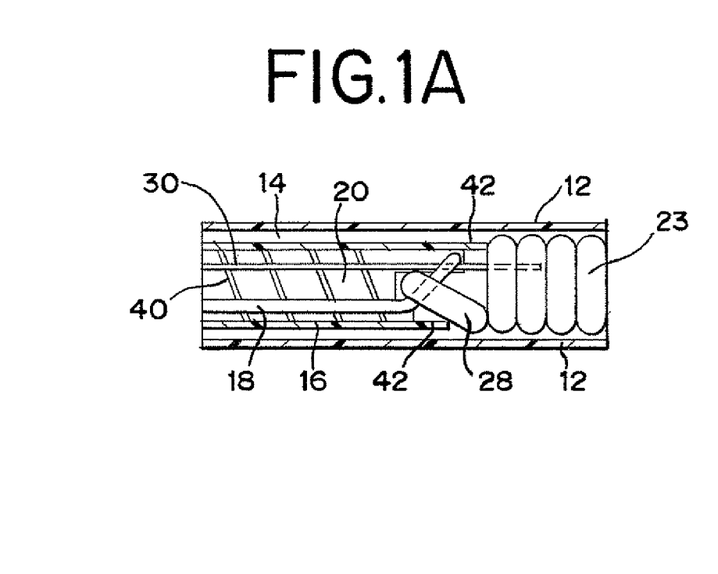
FIG. 1A is a detail view of the distal end of the deployment system of FIG. 1.

FIGS. 1 and 1A generally illustrate one embodiment of a vascular occlusive embolic device deployment system 10 which includes a sheath introducer 12 having a lumen 14 extending therethrough and having an elongated pusher member 16 slidably disposed within the lumen 14 of the sheath introducer 12. An engagement member 18 extends from the pusher member 16 and has an aperture (to be described hereinafter) extending through the distal end thereof. The engagement member 18 may be formed from a distal section of the wall of the pusher member 16 or may be formed as a separate member attached to the distal end of the pusher member 16.

The deployment system 10 also includes an embolic device 23, which as illustrated, may take the form of a helically wound embolic coil, which is disposed in the distal section of the sheath introducer 12. While the embolic device as illustrated is shown as a helically wound coil various other types of embolic devices, such as filaments, braids, foams, expandable meshes and stents, could be delivered using the present deployment system and various other coil configurations could be delivered using this system. A weld, or solder, bead 24 may be formed at the distal end of the embolic device 23 to provide an atraumatic tip for the embolic device. The proximal end of the embolic device 23 includes a retaining ring 28 which extends proximally any may comprise a loop of the embolic device 23 if the embolic device 23 is provided as a coil. Typically, the retaining ring 28 has a central axis which is inclined with respect to the central axis of the sheath introducer 12 and also with respect to the central axis of the embolic device 23, advantageously at an angle suitable for cooperation with the engagement member 18, as shown.

Figure 2:
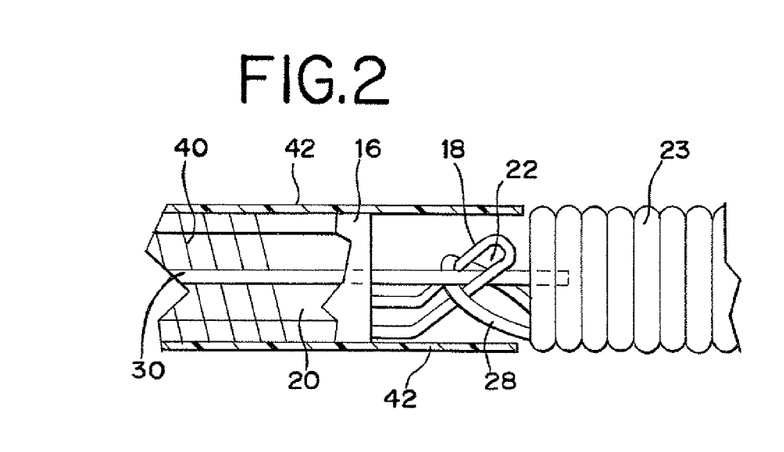
FIG. 2 is a partial cross-sectional view of selected components of another embodiment of an embolic device deployment system according to an aspect of the present invention.

As illustrated in FIG. 2, the engagement member 18 may have a generally L-shaped configuration and extend in part through the retaining ring 28. An elongated detachment member 30 extends from the proximal end of the deployment system 10 and through a lumen 20 in the pusher member 16 and then through the aperture 22 (FIG. 2) of the engagement member 18 and serves the function of interlocking the embolic device 23 to the pusher member 16 until such time as the detachment member 30 is withdrawn proximally.

The detachment member 30 illustratively takes the form of a small diameter elongate filament, however, other forms such as wires or tubular structures are also suitable. In one embodiment, the detachment member 30 is formed of a nickel-titanium alloy, such as nitinol, but other metals and materials such as, stainless steel, PTFE, nylon, ceramic or glass fiber and composites may also be suitable. The components of the deployment system 10 which function to releasably secure the embolic device 23 to the distal end of the pusher member 16 are collectively referred to herein as a mechanical interlocking mechanism. The illustrated mechanical interlocking mechanism includes the engagement member 18 and the detachment member 30, acting in combination with the retaining ring 28 of the embolic device 23, but other mechanical interlocking mechanisms may also be employed without departing from the scope of the present invention.

Figure 3:
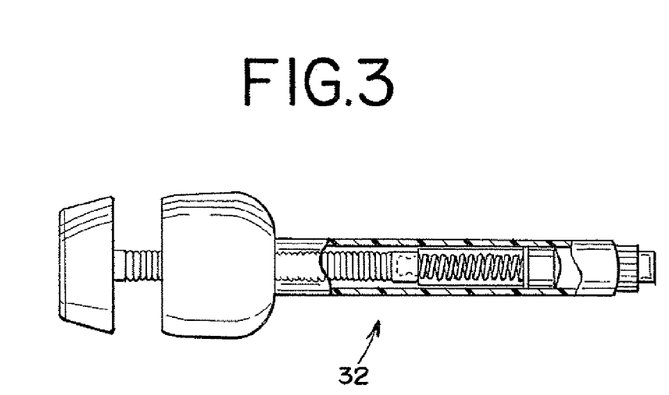
FIG. 3 is a partial cross-sectional view of a fluid pressure source suitable for use with embolic device deployment systems of the present invention.

A fluid pressure source 32 (FIG. 3) is mounted at the proximal end of the pusher member 16, in fluid communication with the lumen 20 of the pusher member 16. In one embodiment, the fluid pressure source 32 comprises a syringe according to known design and adapted to provide a flow of biocompatible fluid, typically saline, through the lumen 20 of the pusher member 16.

Figure 3A:
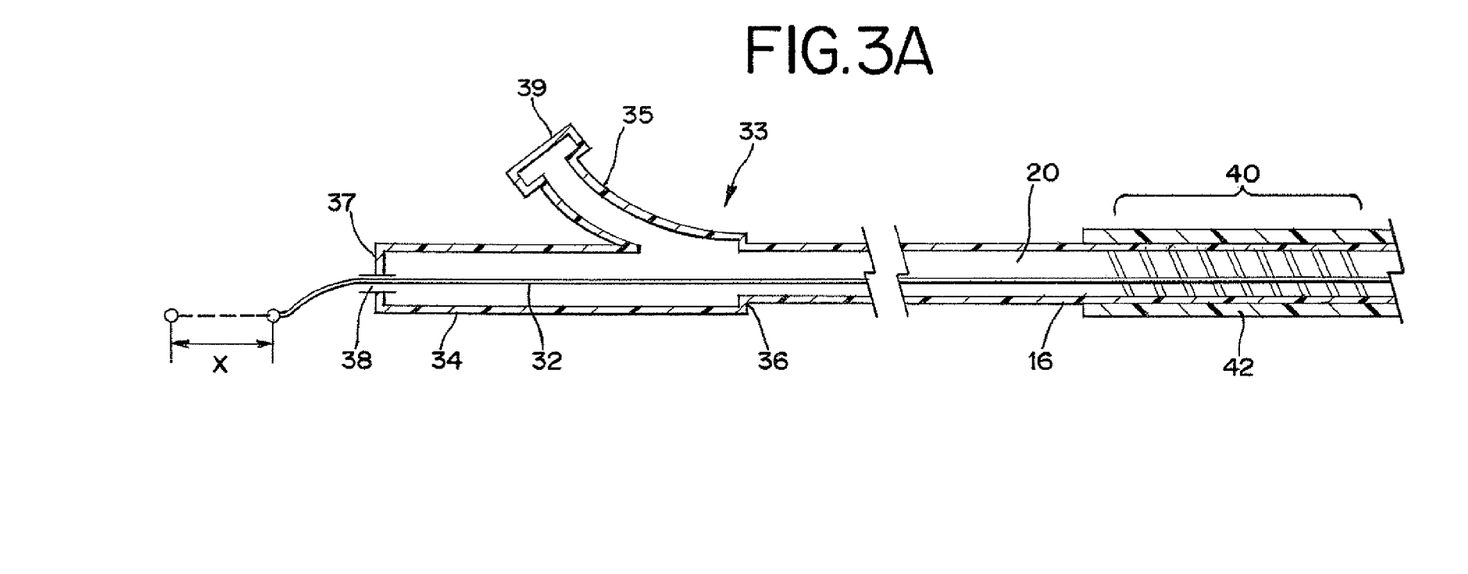
FIG. 3A is a cross-sectional view of selected components of an embolic device deployment system according to an aspect of the present invention and a bifurcated handle suitable for use with the same.

It will be appreciated by those of ordinary skill in the art that both the fluid pressure source 32 and the detachment member 30 are associated at the proximal end of the pusher member 16. To accommodate both components, the deployment system may be provided with a bifurcated handle 33 at the proximal end of the pusher member 16 (FIG. 3A). The illustrated handle 33 remains outside of the body during use and is provided with a first leg 34 to allow manipulation of the detachment member 30, a second leg 35 to allow manipulation of the fluid pressure source 32, and a common leg 36 fluidly connecting the lumen 20 of the pusher member 16 to the first leg 34 and the second leg 35. In one embodiment, the first leg 34 includes a valve 37, such as a one-way valve, having an opening 38 through which the detachment member 30 passes. The valve 37 prevents fluid from leaking from the first leg 34 when the fluid pressure source 32 is actuated. The second leg 35 may include a luer lock 39 adapted to cooperate with a mating luer connector of the fluid pressure source for securing the fluid pressure source to the handle 33.

The pusher member 16 is adapted to channel fluid from the fluid pressure source 32 to the embolic device 23 for deploying the embolic device 23, as will be described in greater detail herein. Thus, it may be advantageous for the pusher member 16 to be substantially continuous, i.e., without any openings between its proximal and distal ends, to avoid fluid leaks and the associated pressure drop. However, it may also be advantageous for the distal end of the pusher member 16 to be relatively flexible for traversing tortuous sections of the vasculature. If the pusher member 16 comprises a metallic hypotube, which may be advantageous to provide a high level of pushability and column strength, flexibility may be imparted to the distal end thereof by a spiral ribbon section 40. The spiral ribbon section 40 comprises a plurality of adjacent turns defined by a helical opening. In one embodiment, the spiral ribbon section 40 comprises a laser cut portion at the distal end of the pusher member 16.

The helical opening of the spiral ribbon section 40 defines a discontinuity in the pusher member 16, which may lead to fluid leaks and a pressure drop during use of the deployment system 10, so it may be advantageous to overlay the outer surface of the spiral ribbon section with a fluid-tight or at least flow-resistant tubular member 42. Suitable tubular members are illustrated in FIGS. 1 to 2. The tubular member 42 of FIGS. 1 and 1A is shown in greater detail in FIG. 1B.

In one embodiment, the tubular member is comprised of a flexible, substantially fluid-tight material, such as polyethylene terephthalate ("PET"). It may be advantageous for the tubular member to be comprised of a shrinkable polymer material, such that it may be slid onto the spiral ribbon section 40 and then manipulated, typically by a heating operation, to radially reduce the tubular member to the extent that it grippingly engages and substantially adheres to the spiral ribbon section 40. Other materials and means of securing the tubular member 42 to the spiral ribbon section 40 may also be employed without departing from the scope of the present invention.

As used in reference to the tubular member, the term "tubular" is not intended to be limiting, but merely refers to a structure having an inner surface suitable for cooperative engagement with the spiral ribbon section 40 to prevent leakage of fluid during use of the deployment system 10. For example, the outer surface of the tubular member need not be strictly cylindrical and/or the tubular member may be provided with either a substantially uniform length in the axial direction (FIG. 2) or an axial length that varies (FIGS. 1 to 1B) without departing from the scope of the present invention. Depending on the configuration of the embolic device 23, it may be advantageous to provide a tubular member having a varying length, as will be described in greater detail herein.

Figure 1B:
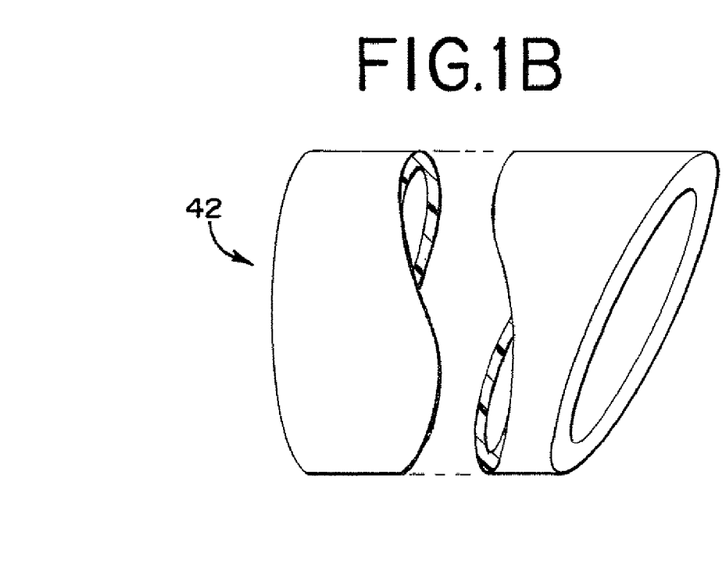
FIG. 1B is a front perspective view of a tubular member of FIG. 1.

The embodiments of FIGS. 1 to 2 show the tubular member 42 extending distally beyond the distal end of the pusher member 16. In such embodiments, the tubular member 42 is effectively an extension of the pusher member 16, as it cooperates with the pusher member 16 to direct fluid flow to the embolic device 23. Therefore, it may be advantageous for the tubular member 42 to extend so as to be directly adjacent to or in non-retentive, abutting relationship to the embolic device 23. If the embolic device 23 has a proximal end that is not perfectly vertical, it may be advantageous for the tubular member 42 to have a different axial length in different sections, such that the profiles of the facing surfaces of the embolic device 23 and the tubular member 42 generally conform to each other. Such a configuration may allow for improved fluid flow because the distal end of the tubular member 42 is directly adjacent to or in non-retentive, abutting relationship to the proximal end of the embolic device 23 at all points. FIG. 1B illustrates one such tubular member, which has a configuration that may be advantageous for use with embolic coils according to known design.

In accordance with the foregoing description, the embolic device 23 is adequately secured to the pusher member 16 by the mechanical interlocking mechanism, so it is unnecessary for the extending tubular member 42 to provide an encircling, retentive relationship as to the embolic device 23.

In use, the introducer 12 is moved through the vasculature until its distal end is adjacent to a target location of a body vessel. The pusher member 16 and the embolic device 23 may be preloaded into the introducer 12, such that they move through the vasculature with the introducer 12, or they may be initially provided separately and ultimately moved through the lumen 14 of the introducer 12 when the introducer 12 has been properly positioned.

Figure 4:
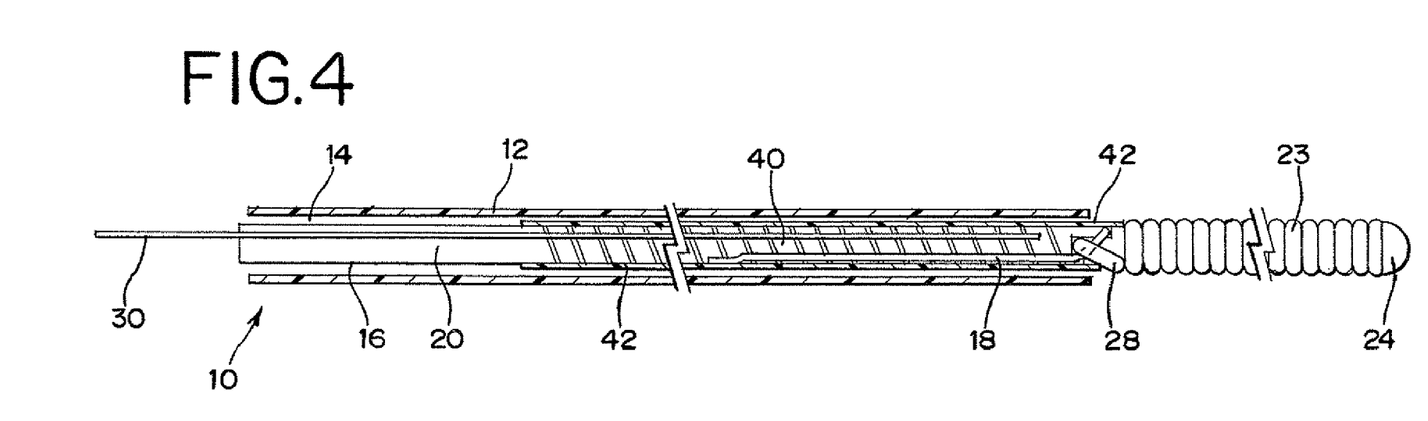
FIG. 4 is a partial cross-sectional view of the deployment device of FIG. 1, with a detachment member of the mechanical interlocking system in a retracted position.
Figure 4A:
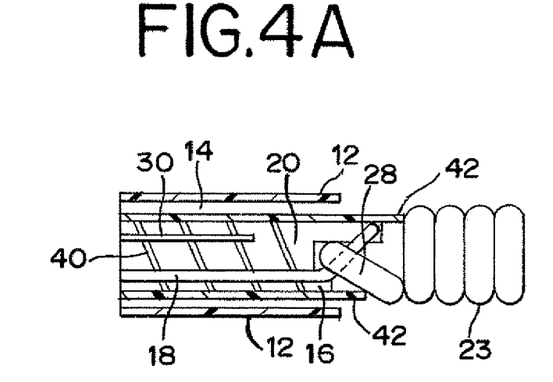
FIG. 4A is a detail view of the distal end of the deployment system of FIG. 4.

FIGS. 4 and 4A illustrate the interlocking arrangement between the embolic device 23 and the pusher member 16 of FIGS. 1 and 1A, however, these figures illustrate the operation of the deployment system once the pusher member 16 has been moved distally (or the introducer 12 has been moved proximally) to a position so that the distal end of the pusher member 16 extends slightly out of the distal end of the sheath introducer 12 or a delivery catheter thereby exposing the embolic device 23.

In one embodiment, radiopaque markers may be secured to the pusher member 16 or the tubular member 42 to assist in accurately positioning the embolic device 23 within a body vessel. If it is determined that the embolic device is improperly positioned, the embolic device 23 may then be withdrawn from that location and placed at another location, or even removed from the body by first withdrawing the pusher member 16 and the embolic device totally back into the delivery catheter. Once the embolic device has been entirely withdrawn back into the delivery catheter, the catheter may then be moved to a more desirable location and the embolic device may then be released at the new location. To enhance the repositionability of the embolic device 23, it may be advantageous to provide it with a stretch resistant member, many of which are known to those having ordinary skill in the art, which allows the embolic device to be withdrawn without concern that it will stretch and become very difficult to remove.

Also illustrated in FIGS. 4 and 4R, once the embolic device 23 has been moved out of the end of the sheath introducer 12 and it has been determined that the embolic device 23 is properly positioned, the detachment member 30 may be pulled proximally to separate the detachment member 30 from the aperture 22 of the engagement member 18 to thereby allow the engagement member 18 to disengage from the retaining ring 28 of the embolic device 23. This is achieved by gripping the portion of the detachment member 30 extending out of the first leg 34 of the bifurcated handle 33 and pulling it a distance "x" (FIG. 3A) sufficient to separate the distal end of the detachment member 30 from the engagement member 18.

Figure 6:
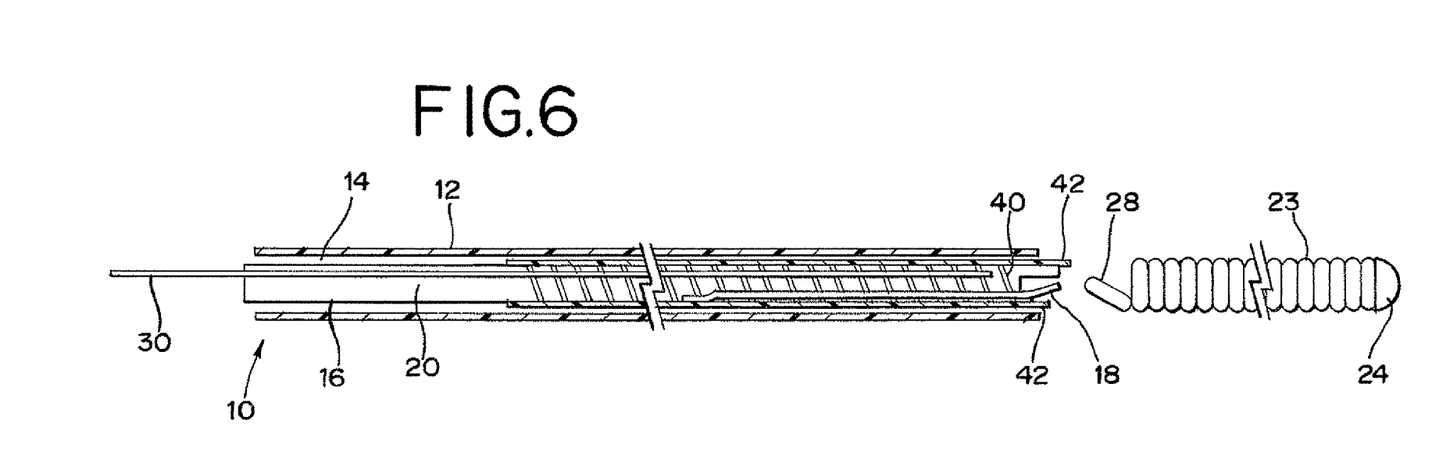
FIG. 6 is a partial cross-sectional view of the deployment system of FIG. 1, with the embolic device in a deployed condition.
Figure 6A:
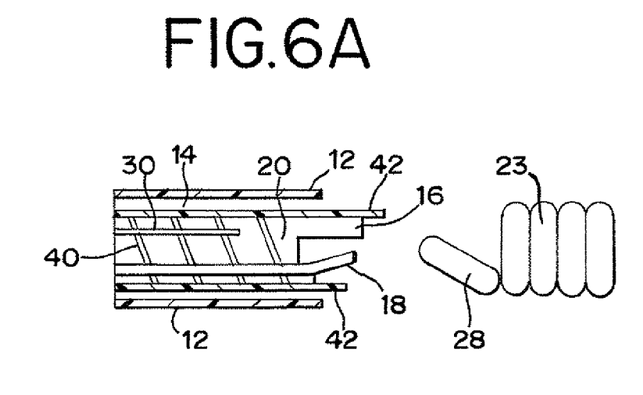
FIG. 6A is a detail view of the distal end of the deployment system of FIG. 6.

To encourage the embolic device 23 to disengage from the mechanical interlocking mechanism, the engagement member 18 may be adapted to deflect away from the retaining ring 28 when the detachment member 30 has been withdrawn. For example, FIGS. 6 and 6A show the engagement member 18 in a relatively straight configuration, deflected out of engagement with the retaining ring 28. This may be achieved using any of a number of methods, such as by providing the engagement member 18 in a normally straight condition and elastically deforming it to interact with the retaining ring 28 and the detachment member 30. In yet another embodiment, the engagement member 18 may be provided as a shape memory material, such as a nickel-titanium alloy, wherein the material is treated to impart a transformation temperature causing the engagement member 18 to automatically bend away from the retaining ring 28 to a default shape (such as a straight configuration or the configuration of FIGS. 6 and 6A) at human body temperature.

Figure 5:
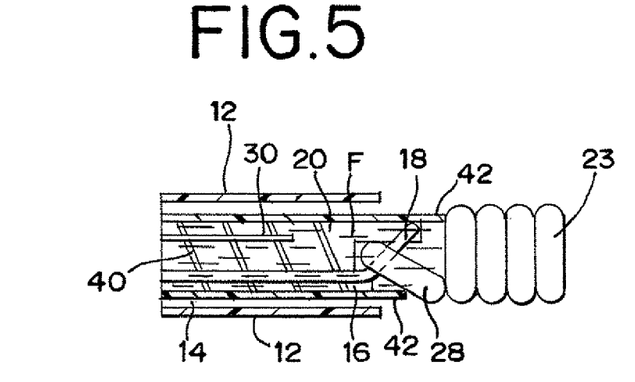
FIG. 5 is a partial cross-sectional view of the deployment system of FIG. 1, with a detachment member of the mechanical interlocking system in a retracted position and fluid pressure applied against the embolic device.

Withdrawing the detachment member 30 may be sufficient to fully deploy the embolic device 23 to the target location of the body vessel, but it has been found that there are times when the application of fluid pressure may be required to fully deploy the embolic device 23. In such situations, the fluid pressure source 32 is actuated to provide a flow of fluid "F" through the lumen 20 of the pusher member 16 (and the portion of the tubular member 42 extending beyond the distal end of the pusher member 16) and against the proximal end of embolic device 23 (FIG. 5). The fluid "F" presses against the embolic device 23, moving it away from the pusher member 16 and to the target location of the body vessel (FIGS. 6 and 6A).

It may be advantageous to provide one or more radiopaque markers on the engagement member 18 to provide visual feedback when the embolic device 23 has been moved away from the pusher member 16. Such radiopaque markers may be obscured by the retaining ring 28 of the embolic device 23 during delivery, such that they are only visible when the embolic device 23 has been released.

Figure 7:
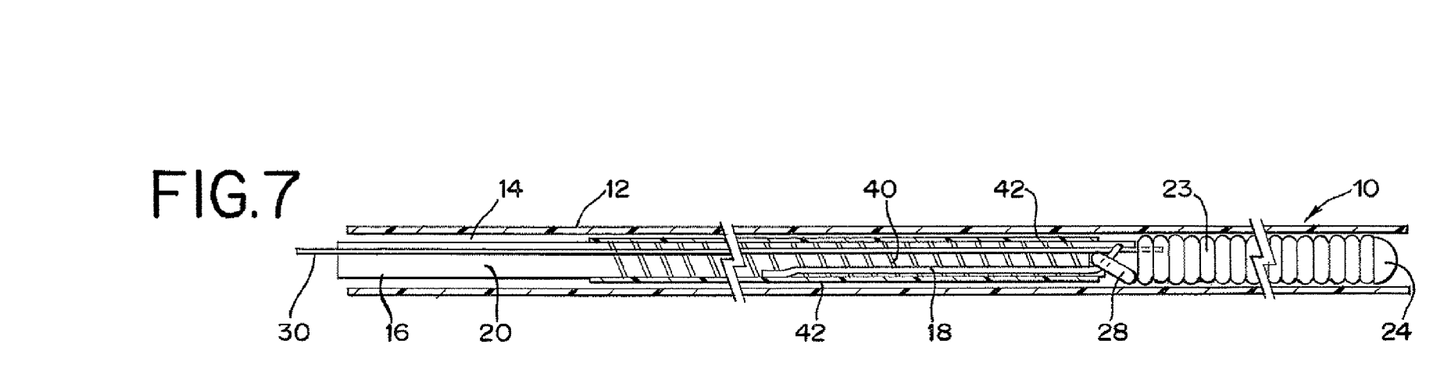
FIG. 7 is a partial cross-sectional view of selected components of another embodiment of an embolic device deployment system according to an aspect of the present invention.
Figures 7A, 7B, 8:
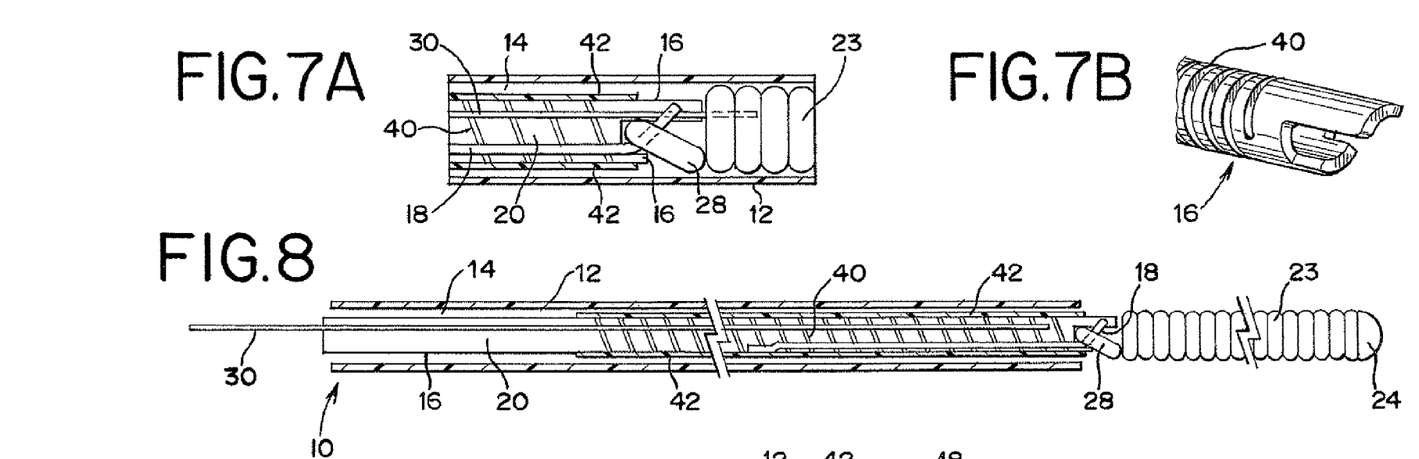
FIG. 7A is a detail view of the distal end of the deployment system of FIG. 7.
FIG. 7B is a front perspective view of the distal end of a pusher member of FIG. 7.
FIG. 8 is a partial cross-sectional view of the deployment device of FIG. 7, with a detachment member of the mechanical interlocking system in a retracted position.

According to another embodiment of a deployment system 10 of the present invention, the distal end of the pusher member 16 may extend distally beyond the tubular member 42, as shown in FIGS. 7 and 7A. This may be achieved using the components of FIG. 1, with the tubular member 42 being positioned farther from the distal end of the pusher member 16, while still overlaying the spiral ribbon section 40. Alternatively, the system may be provided with a shorter tubular member, a pusher member having a longer distal end, or both.

In the embodiment of FIGS. 7 and 7A, the lumen 20 of the pusher member 16 directs fluid flow from the fluid pressure source 32 to the embolic device 23, so the distal end of the pusher member 16 may advantageously extend to be directly adjacent to or in non-retentive, abutting relationship to the embolic device 23. If the embolic device 23 has a proximal end that is not perfectly vertical, it may be advantageous for the distal end of the pusher member 16 to have a different axial length in different sections, such that the profiles of the facing surfaces of the embolic device 23 and the pusher member 16 generally conform to each other. Such a configuration may allow for improved fluid flow because the distal end of the pusher member 16 is directly adjacent to or in non-retentive, abutting relationship to the proximal end of the embolic device 23 at all points. FIG. 7B illustrates the distal end of the pusher member 16 of FIGS. 7 and 7A, which has a configuration that may be advantageous for use with embolic coils according to known design.

In accordance with the foregoing description, the embolic device 23 is adequately secured to the pusher member 16 by the mechanical interlocking mechanism, so it is unnecessary for the extending distal end of the pusher member 16 to also provide an encircling, retentive relationship as to the embolic device 23.

In use, the introducer 12 is moved through the vasculature until its distal end is adjacent to a target location of a body vessel. The pusher member 16 and the embolic device 23 may be preloaded into the introducer 12, such that they move through the vasculature with the introducer 12, or they may be initially provided separately and ultimately moved through the lumen of the introducer 12 when the introducer 12 has been properly positioned.

Figure 8A:
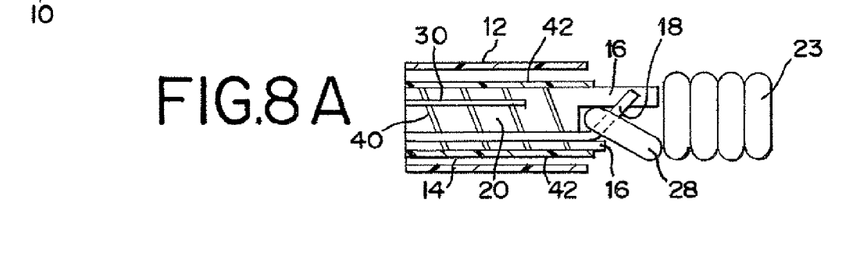
FIG. 8A is a detail view of the distal end of the deployment system of FIG. 8.

FIGS. 8 and 8A illustrate the interlocking arrangement between the embolic device 23 and the pusher member 16 of FIGS. 7 and 7A; however, these figures illustrate the operation of the deployment system once the pusher member 16 has been moved distally (or the introducer 12 has been moved proximally) to a position so that the distal end of the pusher member 16 extends slightly out of the distal end of the sheath introducer 12 or a delivery catheter thereby exposing the embolic device 23. The embolic device 23 may be retracted and repositioned, in accordance with the foregoing description of the embodiment of FIGS. 1 and 1A.

Figure 10:
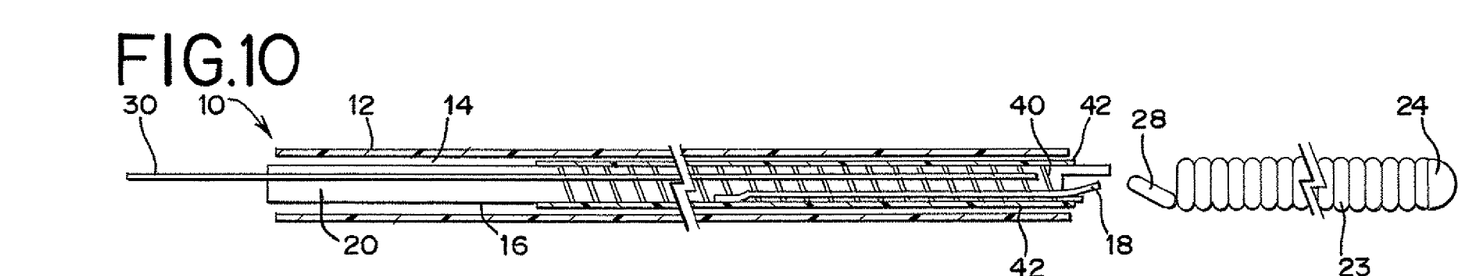
FIG. 10 is a partial cross-sectional view of the deployment system of FIG. 7, with the embolic device in a deployed condition.
Figure 10A:
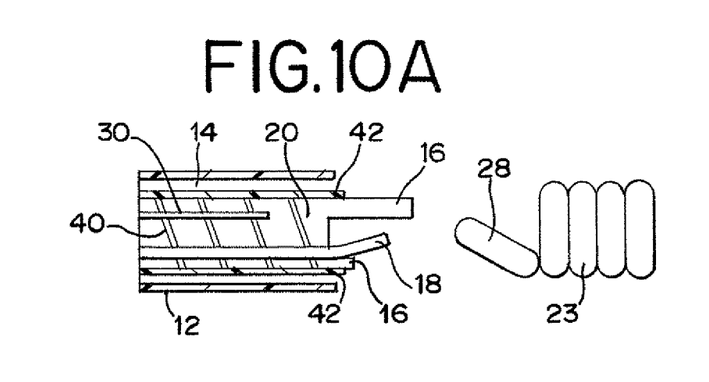
FIG. 10A is a detail view of the distal end of the deployment system of FIG. 10.

Also illustrated in FIGS. 8 and 8A, once the embolic device 23 has been moved out of the end of the sheath introducer 12 and it has been determined that the embolic device 23 is properly positioned, the detachment member 30 may be pulled proximally to withdraw the detachment member from the aperture 22 of the engagement member 18 to thereby allow the engagement member 18 to disengage from the retaining ring 28 of the embolic device 23. The engagement member 18 may be adapted to deflect away from the retaining ring 18 when the detachment member 30 is retracted, as shown in FIGS. 10 and 10A, to encourage the embolic device 23 to detach from the pusher member 16 when the detachment member 30 has been retracted.

Figure 9:
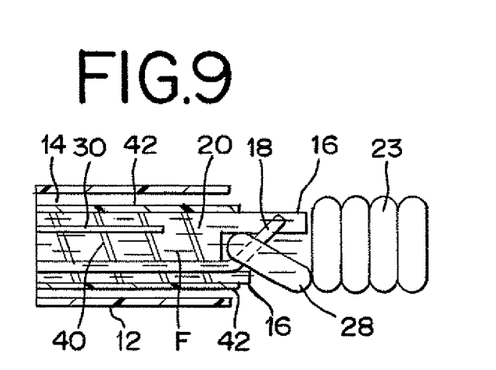
FIG. 9 is a partial cross-sectional view of the deployment system of FIG. 7, with a detachment member of the mechanical interlocking system in a retracted position and fluid pressure applied against the embolic device.

If withdrawing the detachment member 30 is insufficient to fully deploy the embolic device 23 to the target location of the body vessel, the fluid pressure source 32 is actuated to provide a flow of fluid "F" through the lumen 20 of the pusher member 16. The pusher member 16 directs the fluid "F" against the proximal end of embolic device 23 (FIG. 9). The fluid "F" presses against embolic device 23, moving it away from the pusher member 16 and to the target location of the body vessel (FIGS. 10 and 10A).

While the foregoing description has described deployment methods wherein the mechanical interlocking mechanism is disengaged from the embolic device prior to the application of fluid pressure, it is also contemplated that fluid pressure may be employed to disengage the embolic device from the mechanical interlocking mechanism and move the embolic device away from the pusher member.

Figure 11A:
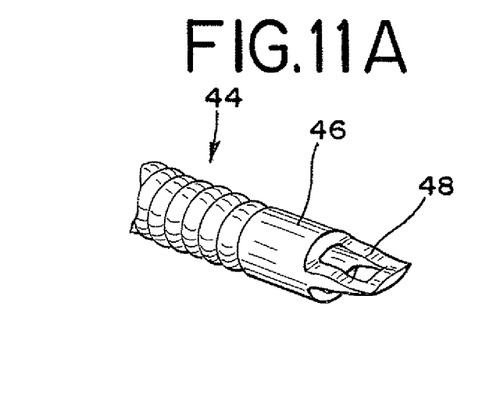
FIG. 11A is a perspective view of a proximal portion of an embolic device having an alternative embodiment of a headpiece suitable for use with the deployment systems of the present invention.
Figure 11B:
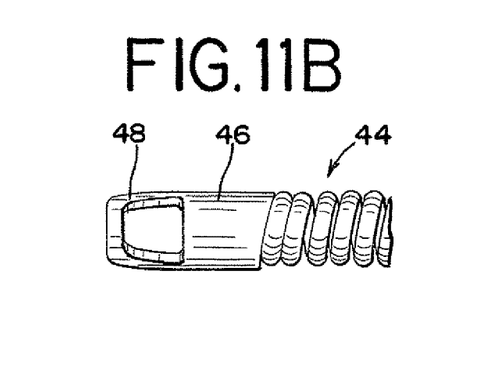
FIG. 11B is a top plan view of the embolic device portion of FIG. 11A.
Figure 11C:
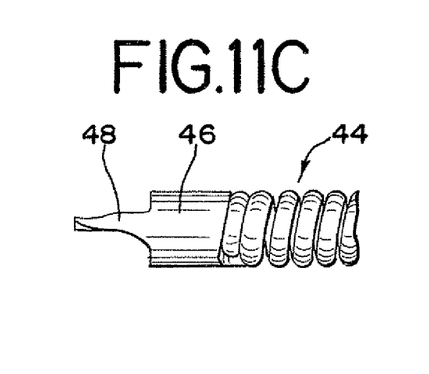
FIG. 11C is a side elevational view of the embolic device portion of FIG. 11A.

According to yet another embodiment of the present invention, an embolic device 44 with a headpiece 46 (FIGS. 11A-11C) may be used in combination with the illustrated mechanical interlocking mechanism, rather than providing the retaining ring as a coil aperture. The illustrated headpiece 46 has a retaining ring 48 with surfaces that are contoured to match the configuration of the engagement member 18, thereby providing a more secure fit.

As is apparent, there are numerous modifications of the preferred embodiment described above which will be readily apparent to one skilled in the art, such as many variations and modifications of the embolic device including numerous coil winding configurations, or alternatively other types of embolic devices. Also, there are many possible variations in the materials and configurations of the release mechanism. These modifications would be apparent to those having ordinary skill in the art to which this invention relates and are intended to be within the scope of the claims which follow.

The invention claimed is:

1. A deployment system for delivering an embolic device to a target location of a body vessel, comprising:
   an elongated flexible deployment catheter having a lumen extending therethrough and having proximal and distal ends;
   an elongated pusher member having a lumen extending therethrough and having proximal and distal ends and being slidably disposed within the lumen of the deployment catheter, at least a portion of the distal end of the pusher member comprising a spiral ribbon section;
   a tubular member engaging and substantially encircling an outer surface of the spiral ribbon section;
   an embolic device releasably secured to the distal end of the pusher member, wherein the tubular member extends distally beyond the distal end of the pusher member to be directly adjacent to or in non-retentive, abutting relationship to a proximal end of the embolic device, and said embolic device includes a retaining ring at the proximal end thereof;
   a mechanical interlocking mechanism for releasably securing the embolic device to the distal end of the pusher member, and said mechanical interlocking mechanism comprises:
      an engagement member extending from the distal end of the pusher member and having an aperture extending through a distal end thereof, a portion of said engagement member extending through said retaining ring, and
      an elongated detachment member extending through the lumen of the pusher member and through the aperture of the engagement member such that when the detachment member is pulled proximally a distal end of the detachment member is withdrawn from the aperture of the engagement member; and
   a source of fluid pressure coupled to the proximal end of the pusher member and in fluid communication with the lumen of the pusher member for upon actuation applying fluid pressure to the lumen and to the embolic device to thereby move the embolic device away from the pusher member.

2. The deployment system of claim 1, wherein said tubular member has a varying longitudinal length extending toward the proximal end of the embolic device.

3. The deployment system of claim 2, wherein the tubular member and the proximal end of the embolic device have surfaces facing each other, and wherein each of said surfaces has a profile generally conforming to the profile of the other.

4. The deployment system of claim 1, wherein the pusher member comprises a metallic hypotube and the spiral ribbon section comprises a laser cut portion of the pusher member.

5. The deployment system of claim 1, wherein the tubular member comprises a shrinkable polymer material.

6. A deployment system for delivering an embolic device to a target location of a body vessel, comprising:
   an elongated flexible deployment catheter having a lumen extending therethrough and having proximal and distal ends;
   an elongated pusher member having a lumen extending therethrough and having proximal and distal ends and being slidably disposed within the lumen of the deployment catheter, at least a portion of the distal end of the pusher member comprising a spiral ribbon section;
   a tubular member engaging and substantially encircling an outer surface of the spiral ribbon section;
   an embolic device releasably secured to the distal end of the pusher member, wherein the distal end of the pusher member extends toward the embolic device to be directly adjacent to or in non-retentive, abutting relationship to a proximal end of the embolic device, and said embolic device includes a retaining ring at the proximal end thereof;
   a mechanical interlocking mechanism for releasably securing the embolic device to the distal end of the pusher member, and said mechanical interlocking mechanism comprises:
      an engagement member extending from the distal end of the pusher member and having an aperture extending through a distal end thereof, a portion of said engagement member extending through said retaining ring, and
      an elongated detachment member extending through the lumen of the pusher member and through the aperture of the engagement member such that when the detachment member is pulled proximally a distal end of the detachment member is withdrawn from the aperture of the engagement member; and
   a source of fluid pressure coupled to the proximal end of the pusher member and in fluid communication with the lumen of the pusher member for upon actuation applying fluid pressure to the lumen and to the embolic device to thereby move the embolic device away from the pusher member.

7. The deployment system of claim 6, wherein the distal end of the pusher member has a varying longitudinal length extending toward the proximal end of the embolic device.

8. The deployment system of claim 7, wherein the distal end of the pusher member and the proximal end of the embolic device have surfaces facing each other, and wherein each of said surfaces has a profile generally conforming to the profile of the other.

9. The deployment system of claim 6, wherein the pusher member comprises a metallic hypotube and the spiral ribbon section comprises a laser cut portion of the pusher member.

10. The deployment system of claim 6, wherein the tubular member comprises a shrinkable polymer material.

11. A method of deploying an embolic device to a target location of a body vessel, comprising:

providing a deployment system having (a) an elongated flexible deployment catheter having a lumen extending therethrough and having proximal and distal ends, (b) an elongated pusher member slidably disposed within the lumen of the deployment catheter and having proximal and distal ends and a lumen, (c) a mechanical interlocking mechanism having an engagement member with an aperture, the engagement member extending from the distal end of the pusher member, (d) an elongated detachment member extending through the lumen of the pusher member and through the engagement member aperture, and (e) an embolic device having a retaining ring at its proximal end, the embolic device being releasably secured to the distal end of the pusher member by a portion of the engagement member extending through the embolic device retaining ring the mechanical interlocking mechanism;

positioning the embolic device generally adjacent to a target location of a body vessel;

disengaging the mechanical interlocking mechanism from the embolic device by proximally pulling the detachment member to withdraw same from the engagement member aperture; and applying fluid pressure through the lumen of the pusher member against the embolic device, thereby moving the embolic device away from the pusher member and releasing the engagement member from the embolic device retaining ring.

12. The method of claim 11, wherein said providing a deployment system includes providing a pusher member having a distal end at least partially defined by a spiral ribbon section, providing a tubular member engaging and substantially encircling an outer surface of the spiral ribbon section, and providing an embolic device releasably secured to the distal end of the pusher member, wherein the tubular member extends distally beyond the distal end of the pusher member to be directly adjacent to or in non-retentive, abutting relationship to a proximal end of the embolic device.

13. The method of claim 11, wherein said providing a deployment system includes providing a pusher member having a distal end at least partially defined by a spiral ribbon section, providing a tubular member engaging and substantially encircling an outer surface of the spiral ribbon section, and providing an embolic device releasably secured to the distal end of the pusher member, wherein the distal end of the pusher member extends toward a proximal end of the embolic device to be directly adjacent to or in non-retentive, abutting relationship to the embolic device.

14. The method of claim 11, wherein said disengaging the mechanical interlocking mechanism from the embolic device precedes said applying fluid pressure through the lumen of the pusher member against the embolic device.

\* \* \* \* \*